United States Patent
Çelik et al.

(10) Patent No.: US 12,138,010 B2
(45) Date of Patent: Nov. 12, 2024

(54) COMBINED WIRELESS AND BODY CHANNEL COMMUNICATION SYSTEM FOR PHYSIOLOGICAL DATA COLLECTION

(71) Applicant: KING ABDULLAH UNIVERSITY OF SCIENCE AND TECHNOLOGY, Thuwal (SA)

(72) Inventors: Abdulkadir Çelik, Thuwal (SA); Ahmed M. Eltawil, Irvine, CA (US)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 36 days.

(21) Appl. No.: 18/028,583

(22) PCT Filed: Sep. 15, 2021

(86) PCT No.: PCT/IB2021/058430
§ 371 (c)(1),
(2) Date: Mar. 27, 2023

(87) PCT Pub. No.: WO2022/064329
PCT Pub. Date: Mar. 31, 2022

(65) Prior Publication Data
US 2024/0016383 A1   Jan. 18, 2024

Related U.S. Application Data

(60) Provisional application No. 63/156,543, filed on Mar. 4, 2021, provisional application No. 63/084,102, filed on Sep. 28, 2020.

(51) Int. Cl.
*A61B 5/00* (2006.01)
*G08C 17/02* (2006.01)
(Continued)

(52) U.S. Cl.
CPC .......... *A61B 5/0024* (2013.01); *A61B 5/0006* (2013.01); *G08C 17/02* (2013.01);
(Continued)

(58) Field of Classification Search
None
See application file for complete search history.

(56) References Cited

U.S. PATENT DOCUMENTS 8,170,656 B2   5/2012   Tan et al.
8,633,809 B2 *  1/2014   Schenk ............... A61B 5/0024
                                                           340/545.4

(Continued)

FOREIGN PATENT DOCUMENTS

KR   101501532 B1 *   3/2015
KR   20200027417 A     3/2020
(Continued)

OTHER PUBLICATIONS

KR-101501532-B1 English Language Translation (Year: 2015).*
(Continued)

*Primary Examiner* — Curtis A Kuntz
*Assistant Examiner* — Jerold B Murphy
(74) *Attorney, Agent, or Firm* — PATENT PORTFOLIO BUILDERS PLLC

(57) ABSTRACT

A physiological data acquisition system includes an array electrode sensor (220) having plural electrodes and configured to acquire physiological data; a single electrode sensor having a single electrode and configured to acquire additional physiological data; and a hub that is configured to receive the physiological data from the array electrode sensor and the additional physiological data from the single electrode sensor only along body communication channels. At least one of the array electrode sensor and the single electrode sensor is configured to send an energy request (Continued)

signal to the hub, along the body communication channels. The hub, in response to the received energy request signal, emits radio frequency signals, which are used by the at least one of the array electrode sensor and the single electrode sensor to harvest energy. Alternatively, the hub may be configured to send a wake up signal to at least one of the array electrode sensor and the single electrode sensor before emitting the radio frequency signals.

20 Claims, 17 Drawing Sheets

(51) Int. Cl.
    *G16H 20/30*     (2018.01)
    *G16H 40/63*     (2018.01)
    *G16H 40/67*     (2018.01)
    *H02J 50/00*     (2016.01)
    *H02J 50/27*     (2016.01)
    *H02J 50/40*     (2016.01)
    *H02J 50/80*     (2016.01)

(52) U.S. Cl.
    CPC ............ *G16H 20/30* (2018.01); *G16H 40/67* (2018.01); *H02J 50/001* (2020.01); *H02J 50/27* (2016.02); *H02J 50/402* (2020.01); *A61B 2560/0214* (2013.01)

(56) References Cited

U.S. PATENT DOCUMENTS

| | | | |
|---|---|---|---|
| 8,811,547 B2* | 8/2014 | Fazzi | .................. H04B 13/005 |
| | | | 375/343 |
| 9,299,248 B2 | 3/2016 | Lake et al. | |
| 9,854,987 B2 | 1/2018 | Chang et al. | |
| 2011/0269414 A1* | 11/2011 | Falck | ...................... H04W 4/80 |
| | | | 455/100 |
| 2014/0217967 A1 | 8/2014 | Zeine et al. | |
| 2018/0241483 A1* | 8/2018 | Park | ........................ H04B 5/266 |
| 2020/0337563 A1* | 10/2020 | Andersen | ............. A61B 5/0031 |
| 2021/0204855 A1* | 7/2021 | Choi | .................... A61B 5/0024 |
| 2021/0233656 A1* | 7/2021 | Tran | ..................... A61B 5/7275 |
| 2022/0095920 A1* | 3/2022 | Mercier | ............... A61B 5/6802 |

FOREIGN PATENT DOCUMENTS

| | | | | |
|---|---|---|---|---|
| WO | WO-2009081343 A1 * | 7/2009 | ........... A61B 5/0024 |
| WO | WO-2010049842 A1 * | 5/2010 | ........... H04B 13/005 |
| WO | WO-2020115378 A1 * | 6/2020 | |

OTHER PUBLICATIONS

WO-2020115378-A1 English Language Translation (Year: 2020).*
International Search Report in corresponding/related International Application No. PCT/IB2021/058430, date of mailing Nov. 29, 2021.
Lee, W., et al., "A Compact Base Station System for Biotelemetry and Wireless Charging of Biomedical Implants," 2019 IEEE Asia-Pacific Microwave Conference (APMC), Singapore, Dec. 10-13, 2019, pp. 339-341, IEEE.
Written Opinion of the International Searching Authority in corresponding/related International Application No. PCT/IB2021/058430, date of mailing Nov. 29, 2021.
Substantive Examination Report in corresponding/related Saudi Arabian Application No. 523440096, dated Mar. 18, 2024.

* cited by examiner

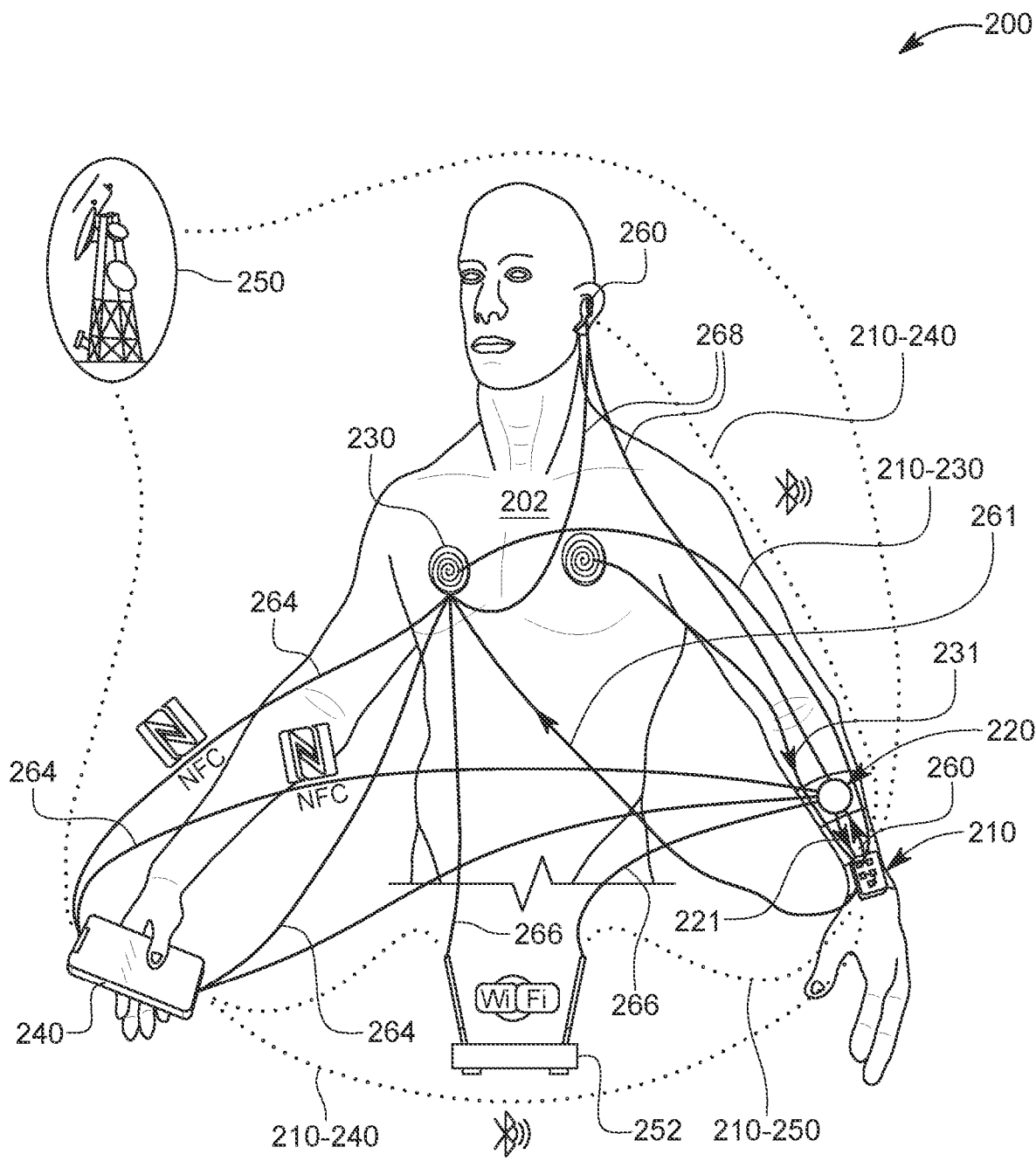
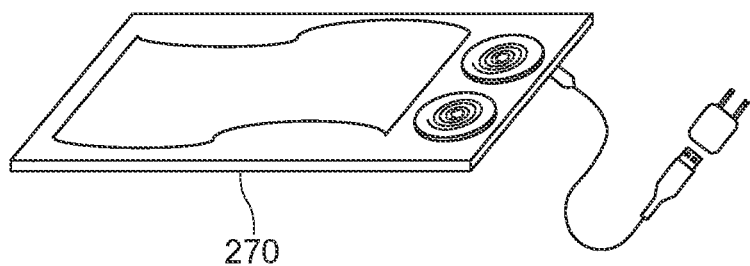

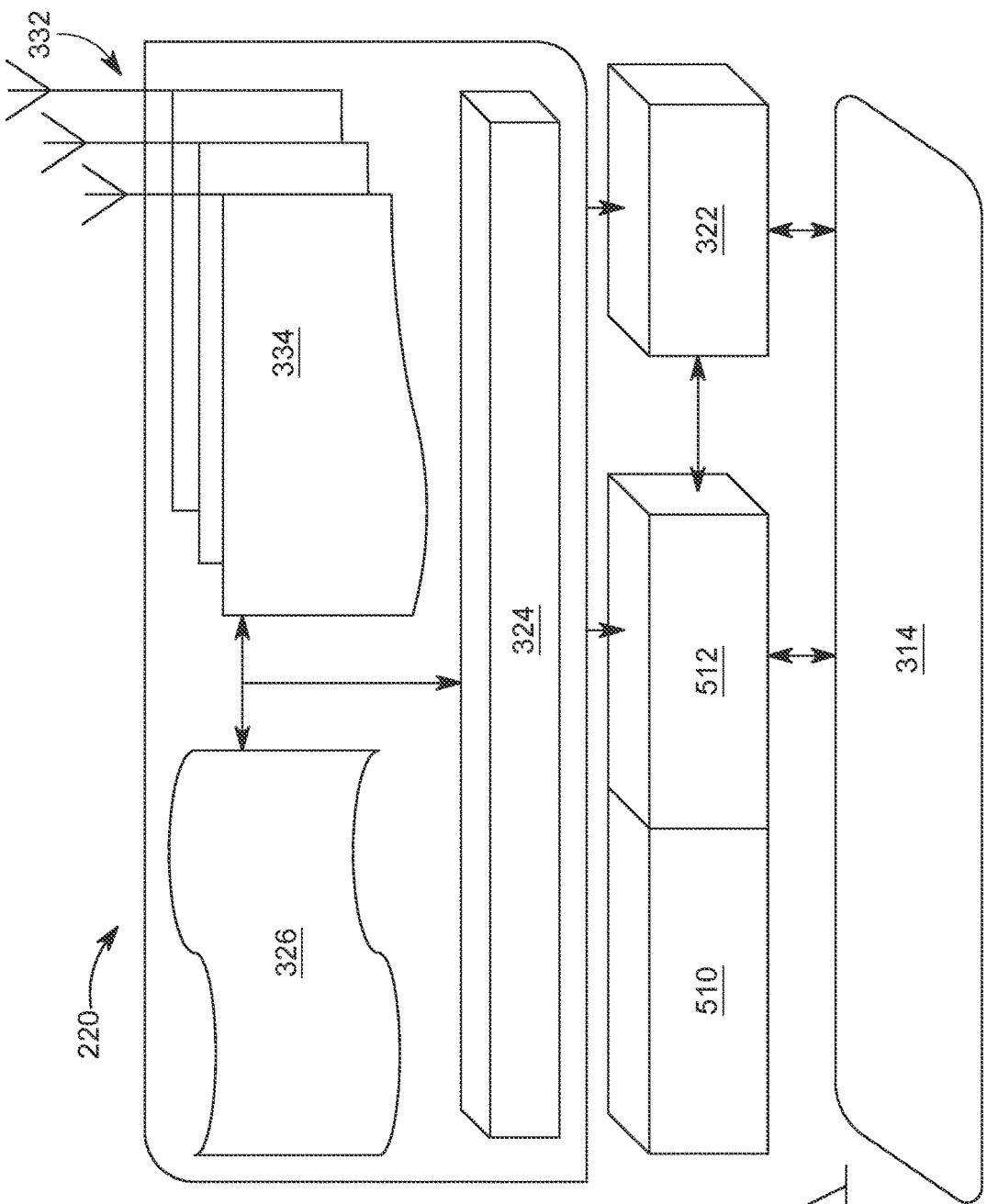
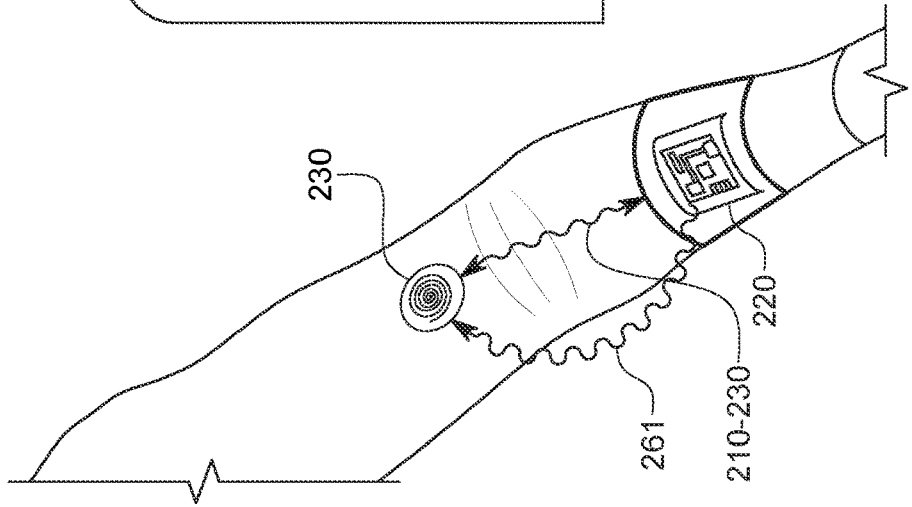
FIG. 5

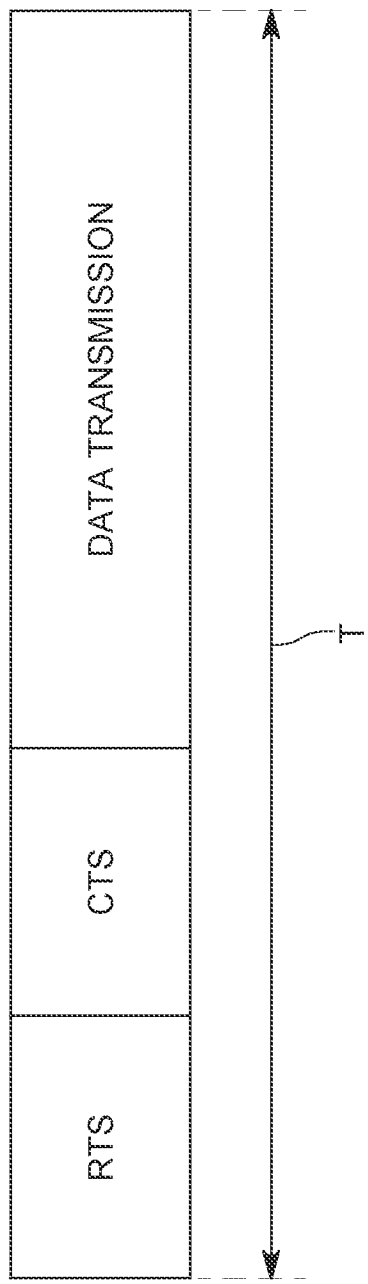

COMBINED WIRELESS AND BODY CHANNEL COMMUNICATION SYSTEM FOR PHYSIOLOGICAL DATA COLLECTION

CROSS-REFERENCE TO RELATED APPLICATIONS

This application is a U.S. National Stage Application of International Application No. PCT/IB2021/058430, filed on Sep. 15, 2021, which claims priority to U.S. Provisional Patent Application No. 63/084,102, filed on Sep. 28, 2020, entitled "WIRELESSLY EMPOWERED ELECTROGRAPHY THROUGH BODY CHANNEL COMMUNICATION ENABLED ELECTRODES AND SMARTWATCH," and U.S. Provisional Patent Application No. 63/156,543, filed on Mar. 4, 2021, entitled "COMBINED WIRELESS AND BODY CHANNEL COMMUNICATION SYSTEM FOR PHYSIOLOGICAL DATA COLLECTION," the disclosures of which are incorporated herein by reference in their entirety.

BACKGROUND

Technical Field

Embodiments of the subject matter disclosed herein generally relate to a system that is attached to the body of a human or animal or a plant for collecting physiological data, and more particularly, to a system that uses the body channel communication for exchanging data among its various components and uses a wireless channel for power and/or commands requirements.

Discussion of the Background

Electrography broadly pertains to the monitoring and recording of electrophysiological signals (e.g., electrograms) obtained through the electrical measurement of ion currents in biological tissues. It is often specified with a particular modality in the pattern of electro-x-graphy (ExG), where 'x' refers to single/several parts, organs, or systems of the body. For instance, electrocardiography (ECG), electroencephalography (EEG), electromyography (EMG), and electropneumography (EPG) relate to electrography of the heart, brain, muscles, and lungs, respectively. As a common practice in human and veterinary medicine, ExG is a standard procedure that involves placing electrodes into/onto the related tissues and collecting electrical signals generated by or affected by the organs or body parts of interest. Based on these acquired electrical signals, specialized personnel (e.g., medical doctors) are able to perform disease prognosis, diagnosis, and treatment. The type, shape, material, and fabrication of the electrodes could differ to meet the underlying application's distinct requirements.

As shown in FIG. 1, electrodes 110 are attached to the skin of an individual 100 and are typically wired to a portable or desktop machine 120, to collect, store, and process received electrograms related to the individual. The cabling complexity and the machine's large size are two main obstacles placed in the way of ExG's daily life and long-term usage. Nowadays, wearable wireless ExG solutions have become commercially available thanks to the recent advances in microelectronics, wireless systems, and signal processing techniques. Commercial off-the-shelf (COTS) solutions typically convey measurements acquired by the sensors 110 to a remote device 130 (e.g., a smartphone) by operating on license-free radio frequency (RF) bands 140, e.g., industrial-scientific-and-medical (ISM) bands. However, the RF communication 140 has the following critical drawbacks:

(1) The Internet of Things (IoT) devices are generally designed to operate on the ISM bands for two reasons: there is no associated fee for the spectrum licensing, and the RF front end modules of the wireless technologies are cheap and readily available. Accordingly, the RF-based ExG modules are susceptible to interference and co-existence issues with the ever-increasing number of IoT devices. This is an essential problem for most of the ExG applications that require ultra-reliable and low-latency communications.

(2) As a result of the RF communications' highly radiative and omnidirectional propagation nature, the RF-based ExG devices inadvertently permit an eavesdropper to intercept or even alter the original data. Thus, it is necessary to guard the confidentiality and privacy of the sensitive physiological information against eavesdropping, overheard, and cyber-attacks of bio-hackers. However, adding extra security measures increases both the hardware complexity and the monetary cost, thus negatively impacting the miniature, low-cost, ultra-low-power design goals.

(3) The radio front end of the RF devices is one of the most complex and power-hungry sub-systems of the RF-based ExG devices. Therefore, they limit the operational lifetime per charging cycle of the sensor and necessitate a larger battery capacity. This naturally requires a larger packaging and more frequent charging, which decreases the quality of user experience and comfort.

Thus, there is a need for a new system that is capable of delivering accurate physiological readings in a confidential manner at a low-cost.

BRIEF SUMMARY OF THE INVENTION

According to an embodiment, there is a physiological data acquisition system that includes an array electrode sensor having plural electrodes and configured to acquire physiological data, a single electrode sensor having a single electrode and configured to acquired additional physiological data, and a hub that is configured to receive the physiological data from the array electrode sensor and the additional physiological data from the single electrode sensor only along body communication channels. At least one of the array electrode sensor and the single electrode sensor is configured to send an energy request signal to the hub, along the body communication channels. The hub, in response to the received energy request signal, emits radio frequency signals, which are used by the at least one of the array electrode sensor and the single electrode sensor to harvest energy.

According to another embodiment, there is a physiological data acquisition system that includes an array electrode sensor having plural electrodes and configured to acquire physiological data, and a smartphone that is configured to receive the physiological data from the array electrode sensor only along body communication channels. The array electrode sensor is configured to send an energy request signal to the smartphone, along the body communication channels, and the smartphone, in response to the received energy request signal, emits radio frequency signals, which are used by the array electrode sensor to harvest energy.

According to still another embodiment, there is a physiological data acquisition system that includes an array electrode sensor having plural electrodes and configured to acquire physiological data, a single electrode sensor having a single electrode and configured to acquired additional physiological data, and a hub that is configured to receive the physiological data from the array electrode sensor and the additional physiological data from the single electrode sensor only along body communication channels. The hub is configured to periodically send a wake up signal to at least one of the array electrode sensor and the single electrode sensor along the body communication channels. The hub, after sending the wake up signal, emits radio frequency signals, which are used by the at least one of the array electrode sensor and the single electrode sensor to harvest energy.

BRIEF DESCRIPTION OF THE DRAWINGS

For a more complete understanding of the present invention, reference is now made to the following descriptions taken in conjunction with the accompanying drawings, in which:

FIG. 2 is a schematic diagram of a wireless data acquisition system that uses body communication channels for transmitting the acquired data and wireless channels for energy harvesting;

FIG. 5 illustrates a configuration of an array electrode sensor that acquires the data and transmits it to the hub along the body communication channels;

FIG. 8 illustrates one possible implementation of a data exchange process between the hub and the sensors of the system shown in FIG. 2;

DETAILED DESCRIPTION OF THE INVENTION

Figure 1:
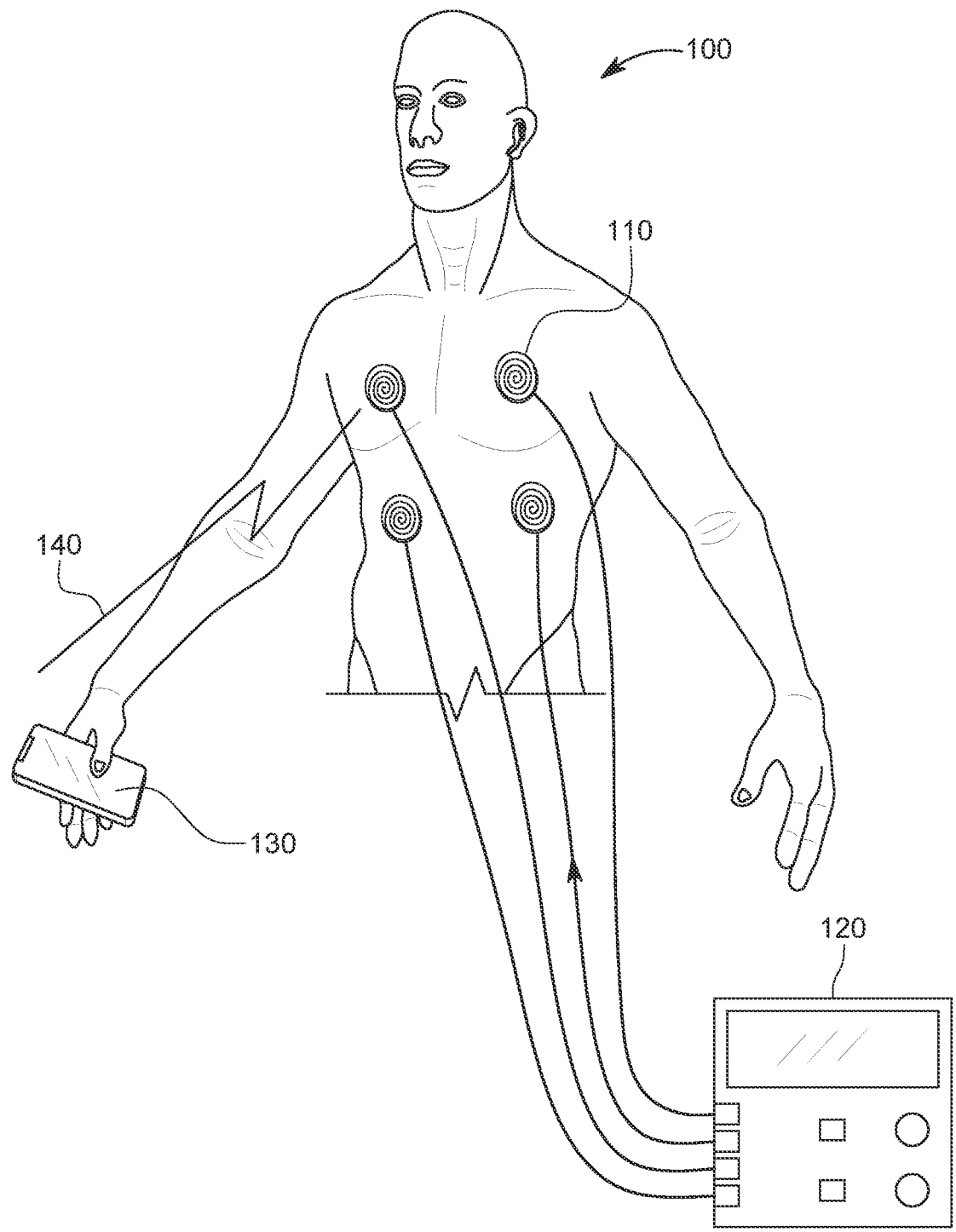
FIG. 1 is a schematic diagram of a wired data acquisition system.

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to an electromyography (EMG) system that is attached to the human body. However, the embodiments to be discussed next are not limited to EMG data or a human body, but they may be applied to the collection of any data (e.g., gait information, lactic acid info, galvanic skin response, etc.) and the sensors may be attached to any object of interest.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, a novel data collecting system includes one or more sensors that communicate with a hub using a body channel communication (BCC) as described in [1] while the hub uses RF communication to exchange data with an external device, e.g., a smartphone or similar computing device. Thus, there are no wires extending from the sensors to the hub or the external device. The sensors are configured to monitor their energy level and to ping the hub when they are low on energy so that the hub can recharge them, through RF signals. Note that the sensors may also be configured to directly collect energy from the environment, without instructions from the hub. The confidentiality of the data acquired by the sensors and transmitted to the hub is ensured by using the BCC communication and the data transmitted from the hub to the external device can be encrypted with the known techniques. One or more of the sensors and/or the hub may be implemented to have a multiple-input multiple-out configuration. This configuration can be dynamically adjusted to balance the BCC transmission of data versus the RF transmission of data and/or power. These features are now discussed in more detail with regard to the figures.

FIG. 2 shows a wireless ExG data acquisition system 200 that includes a hub 210 which is in direct communication with the body 202 of a human, at least one electrode array sensor 220, which is also in direct communication with the body 202, and at least one single electrode sensor 230, which is also in direct communication with the body 202. Each of the sensors 220 and 230 are made of elastic materials and elastic semiconductor devices so that the sensors conform to the human body, i.e., they are easily bendable. Each sensors can be manufactured to have a thickness of less than 100 μm. Technologies for obtaining this type of sensors are disclosed, for example, in U.S. Pat. No. 9,520,293, the entire content of which is incorporated herein by reference.

The hub 210 is configured to control the electrode array sensor 220 and the single electrode sensor 230. Only one hub 210 is used for the system 200 in FIG. 2, and the hub is configured to control all the sensors directly attached to the body 202. However, more hubs may be used if desired. The hub 210 may be configured to communicate in a wireless manner with an external device 240, which is shown in the figure as being a smartphone. In one application, the external device may be a tablet, personal computer, server, or other computing device. Any number of electrode array sensors and single electrode sensors may be placed over the body 202. In one application, the entire system includes only the hub and one electrode array sensor. In another application, the entire system includes only the hub and one single electrode sensor. In yet another application, the system includes the hub and plural electrode array sensors and plural single electrode sensors.

In terms of the type of communications that take place between the various components of the system 200 and also between the one or more components of the system and external devices (e.g., smartphone 240), there are at least two different channels that are employed. The hub 210 communicates with the electrode array sensor 220 and with the single electrode sensor 230 only through BCC channels 210-230, to ensure that no data acquired by the sensors can be intercepted by others or altered. In this way, the privacy of the acquired data is maintained. The BCC is a wireless technology that uses human skin tissues as a communication medium on frequencies ranging from 100 kHz to 100 MHz. The transmitter's electrodes couple electrostatic or magnetostatic fields to the body, which are captured by the receiver's electrodes.

The BCC has the following advantages over the RF counterparts: (1) the human body channel offers a lower propagation loss since it is a better conductor than the air, which naturally yields higher throughputs at very low transmission powers; (2) the BCC has a very negligible signal leakage since it confines the transmission to the human body instead of propagating over the air in the surrounding environment. For this very reason, the BCC offers inherent physical layer security that can provide the necessary privacy and confidentiality required by many ExG applications. Thus, the innate physical layer security features eliminate the need for complex and power-consuming signal processing components and security algorithms, which has positive consequences on previously mentioned design goals; and (3) not lastly, the BCC does not require complex and power-hungry RF-front ends, which naturally increases overall energy-efficiency and reduces the form factor.

The hub 210 communicates with the external device 240 over one or more RF bands 210-240, for example, Bluetooth, Wi-Fi, Cellular, etc. In one application, the hub 210 may communicate directly with a cellular tower 250 or a Wi-Fi enabled device 252 (e.g., router or modem), in addition to the external device 240, also through an RF band 210-240 or 210-250, for example, cellular frequencies. The hub 210 may also communicate using one or more RF bands with other portable devices 260, which are located on the body for other purposes than collecting physiological data, for example, a Bluetooth enabled earpiece or speaker, etc.

Because the sensors 220 and 230 are not connected through wires to the hub or to any other external device, and because these sensors are very small and thin, providing a power source that can provide enough energy to the various electronics that collects and process the data is challenging. The existing wireless sensors, although small and capable of directly being applied to the skin of the body, would not be able to last long when collecting and transmitting the physiological data. To overcome this impediment of the existing sensors, the system 200 is configured to charge the energy storage device of the sensors 220 and 230 on a need basis. More specifically, the sensors 220 and 230 are configured with electronics (to be discussed later) that is capable of monitoring its energy storage device, and when detecting that the stored energy is below a given threshold, that sensor will ping the hub, i.e., send an energy request signal 221 or 231 to the hub 210, through the BCC channel 210-230, to request energy. Alternatively or in addition, if the hub 210 does not hear from a given sensor, it will send a pulse of energy to the sensor to wake up the sensor, and inquire about the sensor's energy status. In response to this request, the hub 210 is configured to generate an RF signal 261, on a dedicated band that is known to the sensor, and the sensor is equipped with an antenna and corresponding electronics for receiving the RF signal 261, and transforming the energy of the signal into electrical energy, which is then stored by the energy storage device of the sensor. In this way, although the original energy storage device of the sensor is limited, using the above mentioned mechanism, it is possible to recharge the energy storage device as many times as necessary to extend the life of the sensor for as long as it is needed.

It is noted that the sensors 220 and 230 may also be configured to receive RF signals 264, 266, and/or 268 (e.g., near field communication technology) directly from the external devices 240, 252, and 260, as schematically illustrated in FIG. 2. These RF signals may also be used by the sensors to recharge their energy storage devices. However, the difference between recharging the energy storage device from RF signals sent by the hub 210 and RF signals sent by ambient devices is that the sensor can rely on the RF signals from the hub, as the sensor can control when to initiate the generation of the RF signal 261 and rely on its availability when in need. That is not the case when the sensor relies on the ambient devices as these devices are neither communicating with the sensor, nor controlled by the sensor. In other words, the timing of the energy charging of the sensor from the energy emitted by the hub is initiated and/or controlled by the sensor, based on the sensor's needs. In one application, the timing of the generation of the energy for charging the sensor is initiated and/or controlled by the hub. FIG. 2 also shows a wireless charging pad 270 that may be used to recharge any of the components of the system 200.

Based on the configuration described herein, the system 200 is a wireless ExG (WExG) system which has a central hub 210 that communicates wirelessly over the body channel with the various sensors 220 and 230 and the sensors charge wirelessly through RF energy harvesting (RF-EH) technology. The hub 210 can conduct WExG over electrodes placed in its strap and casing as discussed next. The sensors may also be used for BCC to aggregate and disseminate data/control packets from/to sensors placed in various body locations, i.e., sensors 230 can send data to sensor 220, sensor 220 aggregates this data and sends it to the hub 210. That is, the hub plays the role of a manager that orchestrates the overall WExG procedure. The hub is also capable of sharing raw or processed WExG data with authorized authorities (e.g., external devices 240 or 250 or 252) though RF-based off-body communication technologies, such as Wi-Fi, Bluetooth, Cellular, etc.

Figure 3A:
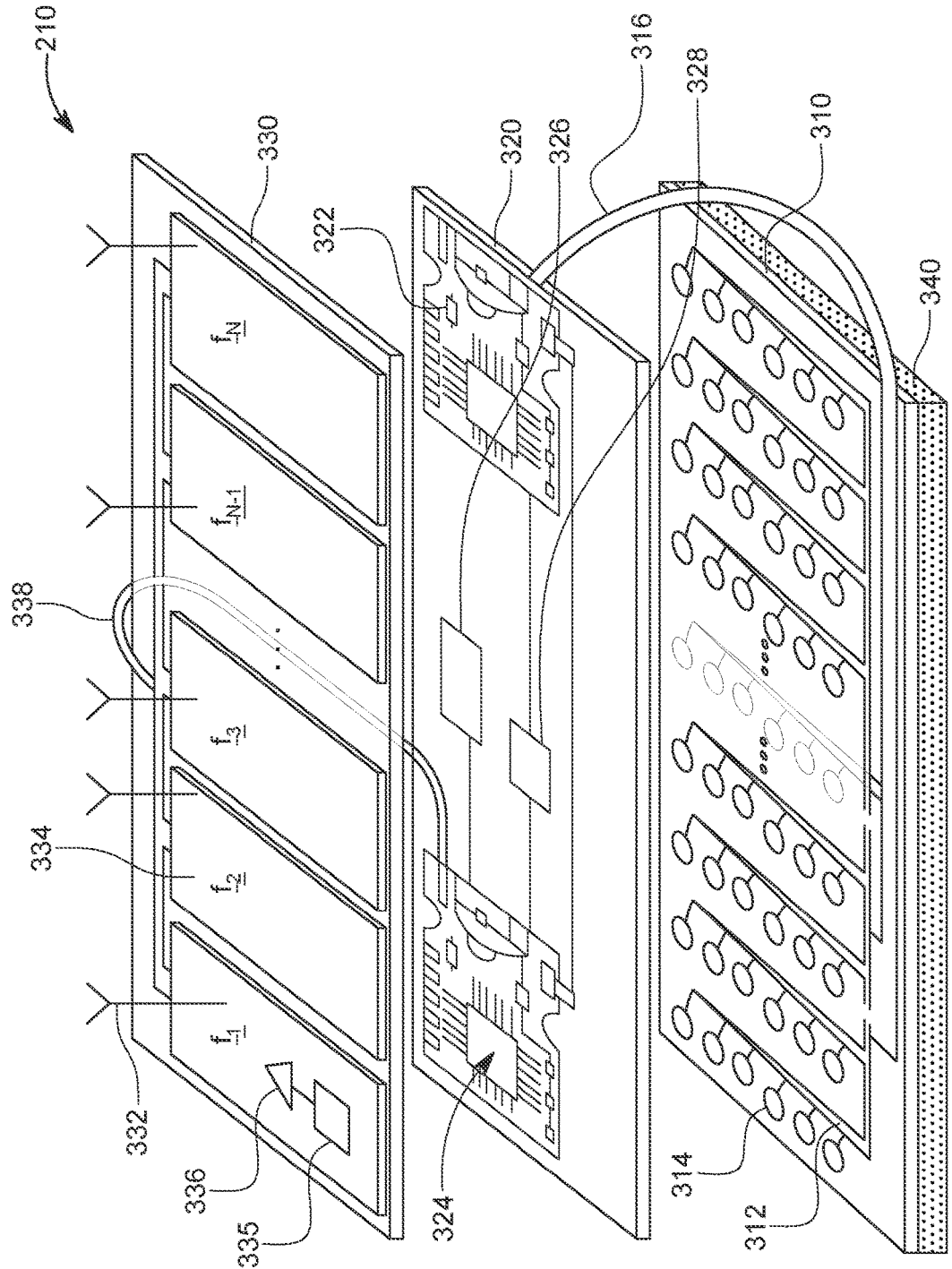
FIGS. 3A to 3C illustrate an internal configuration of a hub of the system of FIG. 2.
Figure 3B:
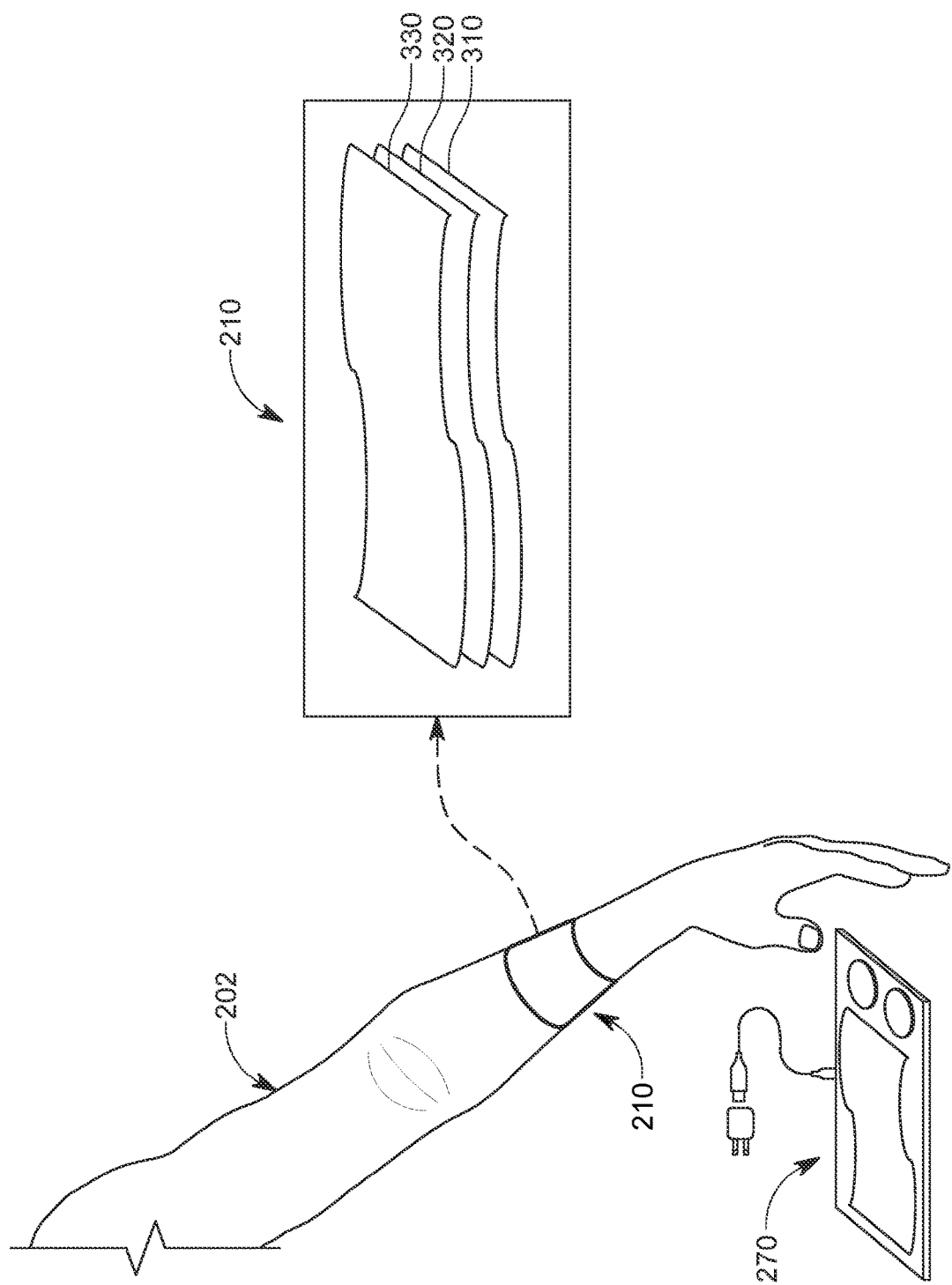

The specific structures of the various components of the system 200 for achieving the functionalities discussed above are now discussed in more detail. The electrode array sensor 210 is illustrated in FIGS. 3A and 3B as having three layers 310, 320 and 330 formed on top of each other. The three layers are made of flexible materials so that the entire sensor 210 is conformal, i.e., follow the shape of the part of the body to which the sensor is attached. A glue or sticky layer 340 may be used to attach the sensor 210 to the body 202. The first layer 310 is the electrode array layer, which includes K×M flexible electrodes 314, where K describes the number of branches 312 and M describes the number of pads or electrodes 314 attached to each branch 312. Note that all the branches are connected to a BCC module 322, which is located on the second electronics layer 320, either independently or together. In other words, it is possible for the BCC module 322 to independently control each branch of the K×M flexible electrodes 314 for purposes to be discussed later. This means that the cable 316 that connects the branches 312 to the BCC module 322 on the electronics layer 320 may include plural wires, and each wire is uniquely attached to one or more branches, for ensuring that the one or more branches are controlled independent of the other branches. The K×M electrode array is configured to measure electrograms and transmit/receive communication signals to the BCC module 322. The array is configured to have adaptive impedance sensing and matching circuits to improve the quality of both sensing and communication channels.

The electrodes can simultaneously be used for both WExG data acquisition and BCC communication, at low (f<500 Hz) and high (100 KHz<f<100 MHz) frequencies, respectively. A processor 328 is connected to the BCC module 322 and is configured to control/process the acquired physiological data. In one embodiment, the processor may perform pre-processing of the data, for example, analog to digital processing. The processor 328 can generate an energy request signal or other commands and instruct the BCC module and the electrodes 314 to send the signal or commands to the hub 210, along the BCC channels. The processor 328 can also decide when and how to transfer the acquired physiological data to the hub 210, by using the BCC module 322 and the electrodes 314.

The flexible multi-band patch rectenna layer 330 is configured to receive RF signals over N radio antennas 332, where N is an integer equal to 1 or larger. One or more antennas of the N antennas are dedicated to one of R specific RF bands (R can be any non-zero natural number). The antennas has a design selected to maximize the antenna gain for that band. The received RF signal (from the hub or another ambient device) is then fed into a multi-band rectenna 334, which has a pair of matching circuit 335 and rectifier 336 to convert the RF signals to a direct current at each band, in parallel. The generated direct current is then provided to the electronics layer 320, along a corresponding power cable 338.

The electronics layer 320 includes a power block 324, which is connected to the power cable 338 and is configured to combine the converted energy from each band and store it into an energy storage device 326, for example, a flexible and thin layer of solid-state super-capacitor (S3C). The design and fabrication of the S3C 326 allows harvesting RF power with minimal time delay and allows the consumption of the stored energy with no limitation. The power block 324 is responsible for distributing the power to the below sub-components (e.g., branches and electrodes, and the processor and the BCC module) and may use one or more power efficiency algorithms to maximize the overall device lifetime. The processor 328 is configured to monitor the energy stored in the energy storage device 326, and to generate the energy request signal 231. Further, the processor 328 instructs the BCC module 322 to send the energy request signal 231 to the hub 210 through one or more of the electrodes 314.

Figure 3C:
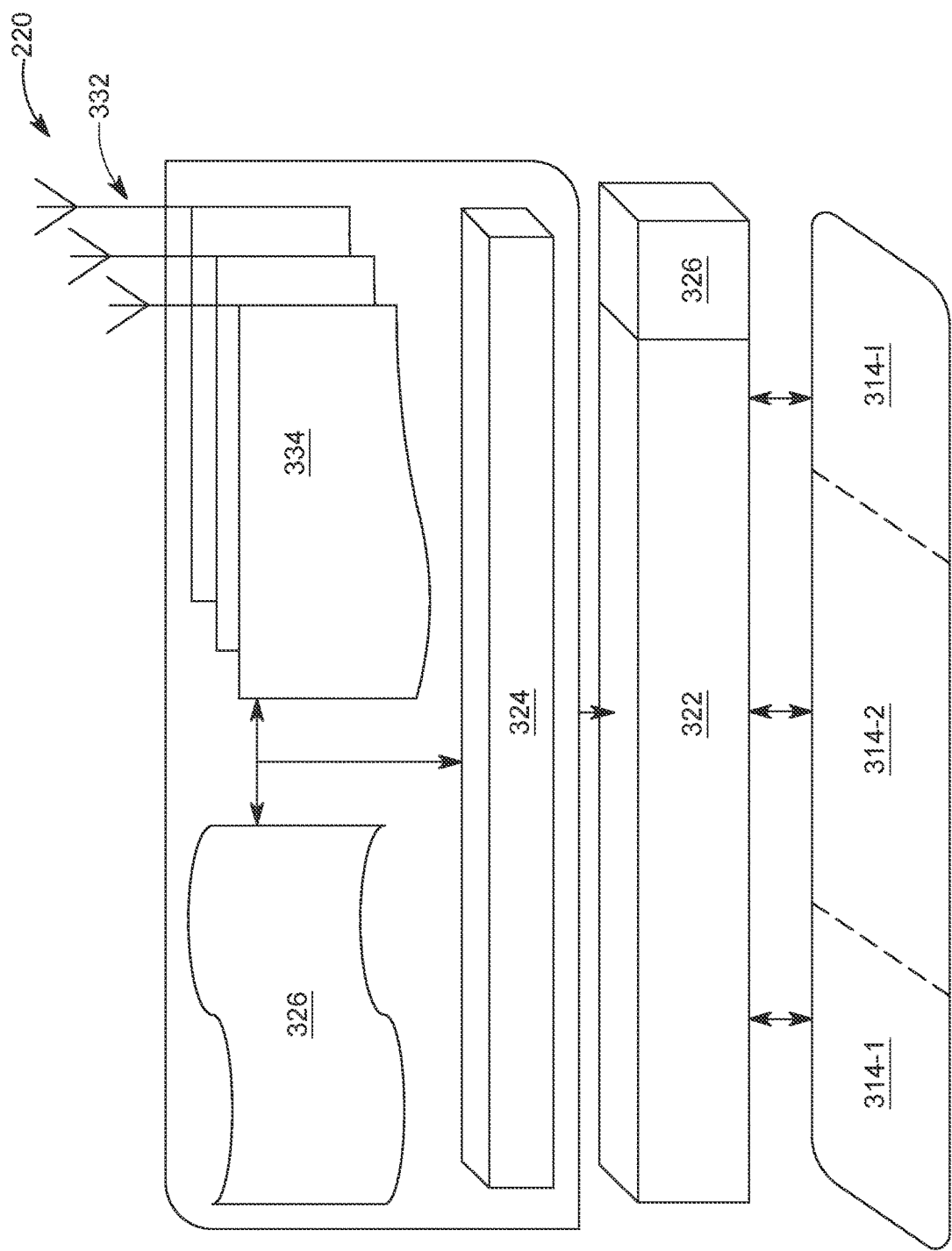

Leveraging the availability of the multiple electrodes 314 enable the sensor 220 to achieve multi-input multi-output (MIMO)-BCC communication with the hub 210. Accordingly, the BCC module 322 may be configured with algorithms used in the telecommunications for implementing MIMO-BCC between the sensor 220 and the hub 210. In one application, the processor 328 or the existing processors of the power module 324 or the BCC block 322 may be configured to select a first subset 314-1 (see FIG. 3C) of the electrodes 314 for exchanging data with the hub 210, and a second subset 314-2 (see FIG. 3C) of the electrodes 324 for acquiring the physiological data. The two actions can be performed independently and simultaneously as the electrodes are independently controlled by the processor 328. In this respect, FIG. 3C illustrates the block configuration of the sensor 220 and the possibility to use plural subsets 314-I of the electrodes 314 for different purposes, i.e., collection of a first type of data, collection of a second type of data, and transmission of the data to the hub along BCC channels. Other combinations of functionalities of these electrodes may be implemented in the sensor 220. In one application, at least one electrode 314 may be used as a ground electrode.

Figure 4:
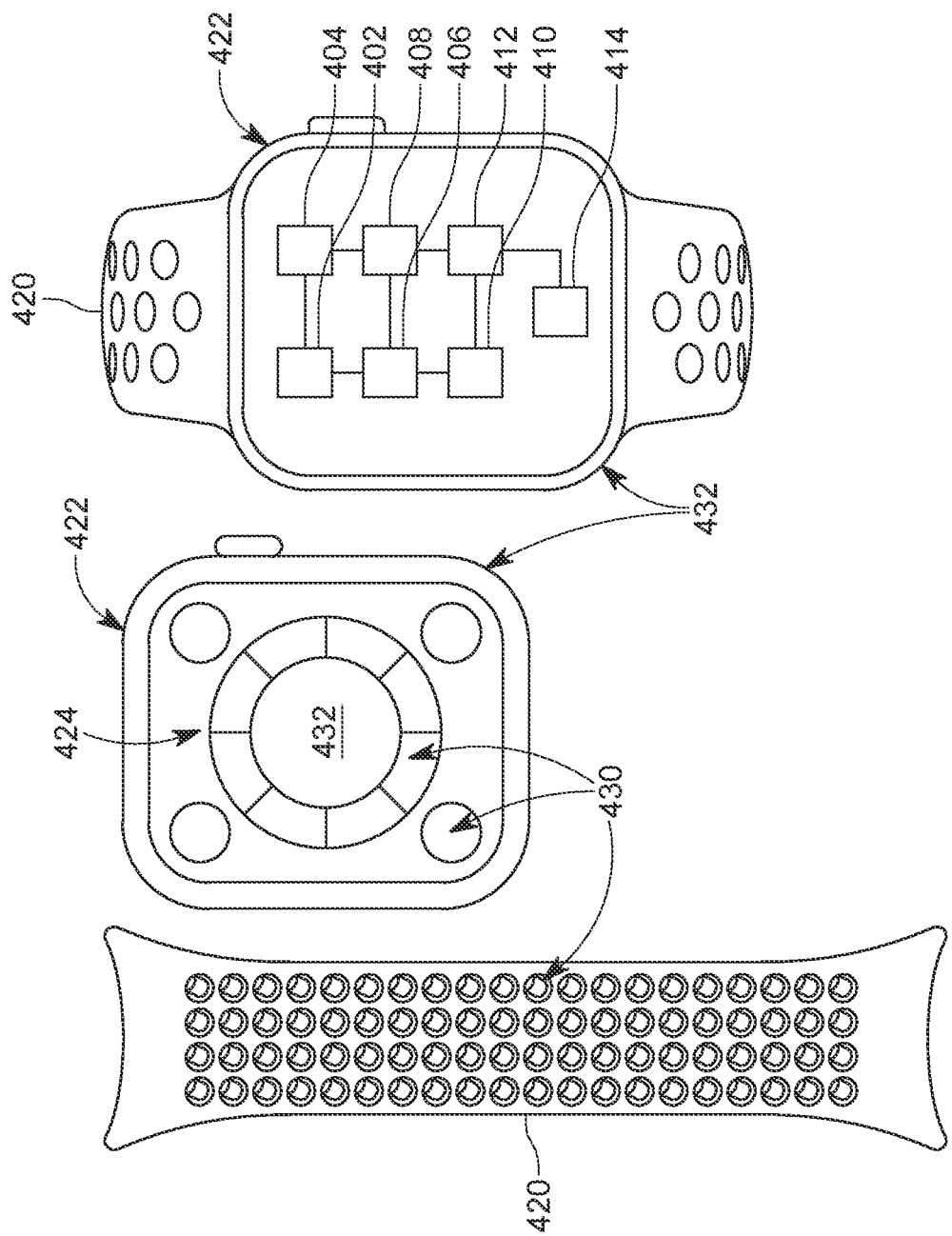
FIG. 4 illustrates an external configuration of the hub shown in FIGS. 3A to 3C.

The configuration of the hub 210 is illustrated in FIG. 4. The hub 210 is shown in the figure as being implemented as a smartwatch. The hub 210 may include one or more of a processor 402, a memory 404, a GPS system 406, a power supply 408, an RF transceiver 410, a BCC transceiver 412 and other known electronics 414, e.g., RF antenna. A strap 420 is used to connect the casing 422 of the hub 210 to the body 202. In one embodiment, the casing 422 holds all the above components. On the back 424 of the casing 422, and/or on the strap 420, plural electrodes 430 are placed for the BCC communication. These electrodes 430 are in addition to the electrodes 432 that a traditional smartwatch has. It is noted that some of the electrodes 430 may be placed directly on the strap 420. In one embodiment, at least one reference or ground electrode 432 is present. The ground electrode 432 may be attached to the casing 422 and/or may be placed on the strap 420.

The hub 210 is configured to play several roles: 1) the WExG measurements require a reference electrode placed on an electrically neutral tissue. Thus, the hub 210 having the reference electrode 432 eliminates the need for a separate electrode by acting as a reference; 2) the hub 210 has its own arrays of electrodes 430 placed in the strap 420 and/or the casing 422. Hence, it can cooperate with the electrode array sensor 220 to improve the overall measurement performance; and 3) as the hub typically performs off-body communications over several RF-bands (Bluetooth, Wi-Fi, Cellular, etc.), its close proximity to the sensors 220 and 230 provide a desirable amount of RF-EH.

As previously discussed, the hub can respond to an energy request signal from one or more sensors to intentionally use one or more of RF bands to perform on-demand wireless charging of the sensors. This capability can be implemented to be controlled by the processor of the hub, or by the processor of the requesting node. If the first approach is taken, then the processor 402, upon receiving the energy request signal from the sensor 220 or 230, checks its energy level and, if this level is about a certain threshold, then the processor switches on the RF generator and generates the RF signal 261 to send RF energy to the requesting sensor. If the second approach is taken, then the processor 328 of the sensor 220 instructs the hub to generate the RF signal 261 and the hub obeys these instructions. Similar to the electrode array sensor 220, the smartwatch 210's plural electrodes 430 can also be used simultaneously for both WExG data collection and BCC communication. Thus, the availability of multiple electrodes at both the electrode array sensor 220 and at the smartwatch 210 enables MIMO-BCC between them.

In the absence of a hub, a communication and computing module 510 can be embedded on top of the array electrode sensor 220, as illustrated in FIG. 5. For this case, the measurements obtained by the BCC module 322 are processed and shared by a Bluetooth low energy (BLE) transceiver 512 with an external device (not shown). For this specific case, because there is no hub, there should be at least one reference electrode for reference purposes, and the reference electrode may be implemented with the single electrode sensor 230. For this case, the communication and computing module 510 may emit RF signals 261 to recharge the energy storage device of the single electrode sensor 230, similar to the mechanism discussed above for the array electrode sensor 220.

Figure 6:
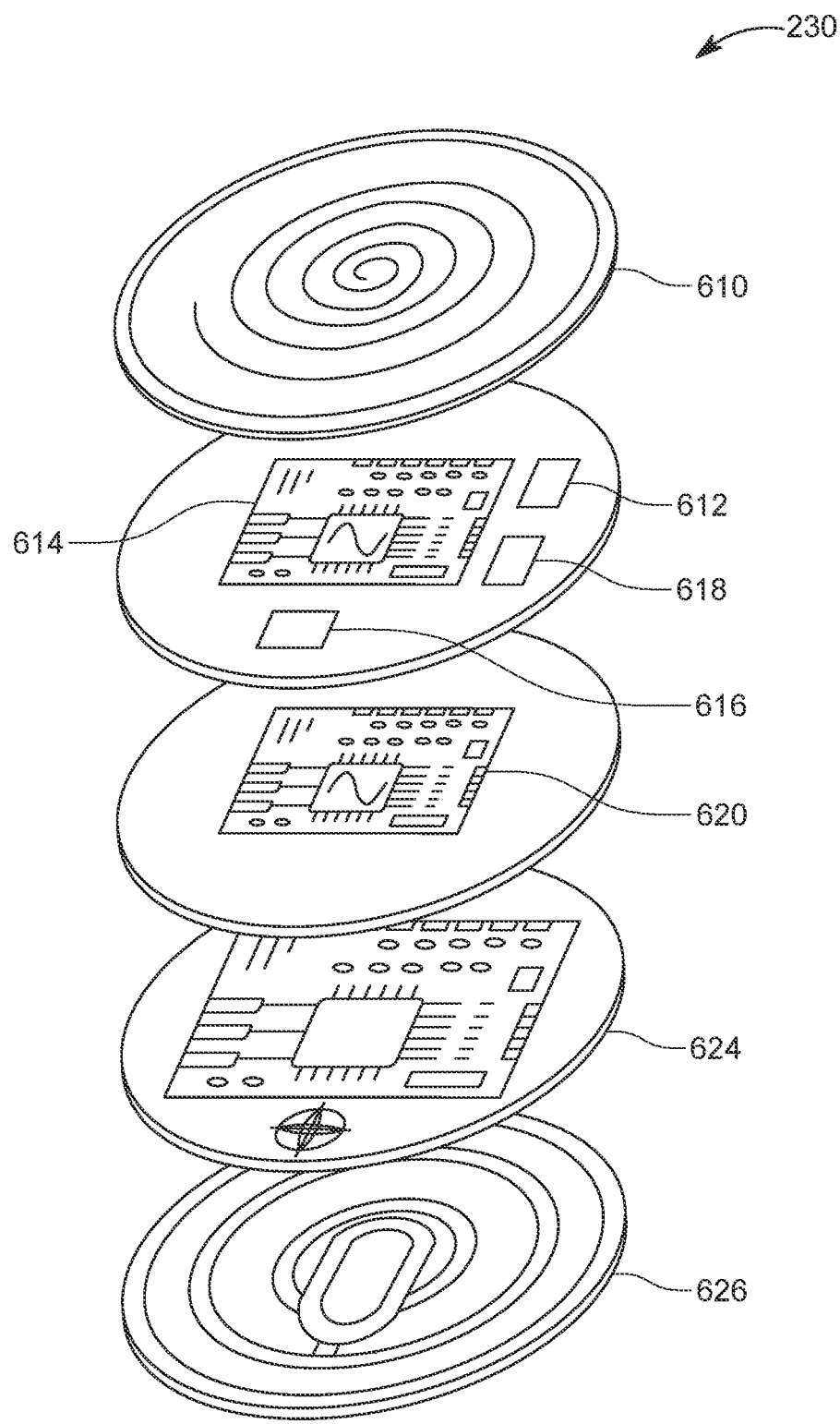
FIG. 6 illustrates a configuration of a single electrode sensor that acquires additional data and transmits it to the hub along the body communication channels.

The configuration of the single electrode sensor 230 is illustrated in FIG. 6 and has a layered structure, where each layer is made of flexible electronics. As shown in the figure, the sensor 230 can be regarded as a miniature version of the sensor 220, with the following differences:

(1) Unlike the sensor 220, the sensor 230 has a single wideband antenna 610 shared by all matching circuit and rectifier pairs 612, which are designed to operate on a specific band. The received signal is then fed into a multi-band rectenna, which has a pair of matching circuit and rectifier 612 to convert the RF signals to direct current power, at each band in parallel. A power block 614 combines the converted energy from each band and stores it to an energy storage device 616, for example, a flexible and thin layer S3C. The design and fabrication of the S3C 616 allow harvesting RF power all the time with minimal time delay and also allows the consumption of stored energy with no limitation. The power block 614 is responsible for distributing power to the other subcomponents and employs various power efficiency algorithms to maximize the overall device lifetime. A single-input single-output (SISO)-BCC modem 620 is responsible for modulation and transmission of the measurements provided by the sensor block 624. The sensor block 624 receives measurements from the single electrode 626. The single electrode 626 is configured to directly contact the body 202 and measure electrograms and transmit communication signals. It may include adaptive impedance sensing and matching circuits to improve the quality of both sensing and communication channels. It is noted that in one embodiment, the single electrode sensor 230 is configured to transmit signals only along BCC channels, but to receive signals along both BCC and RF channels. In this embodiment, the RF signals are used to harvest energy and the BCC signals are for exchanging data, e.g., acquiring physiological measurements, and/or receiving or sending commands. The single electrode sensor 220 may include a processor 618 that is configured to determine the energy left in the energy storage device 614, and instruct the modem 620 to use the electrode 626 to send the energy request signal 231 to the hub 210 or the sensor 220, along the BCC channels. The processor may also use the modem 620 and the electrode 626 to send the acquired physiological data to the hub 210, also along the BCC channels.

Figure 7:
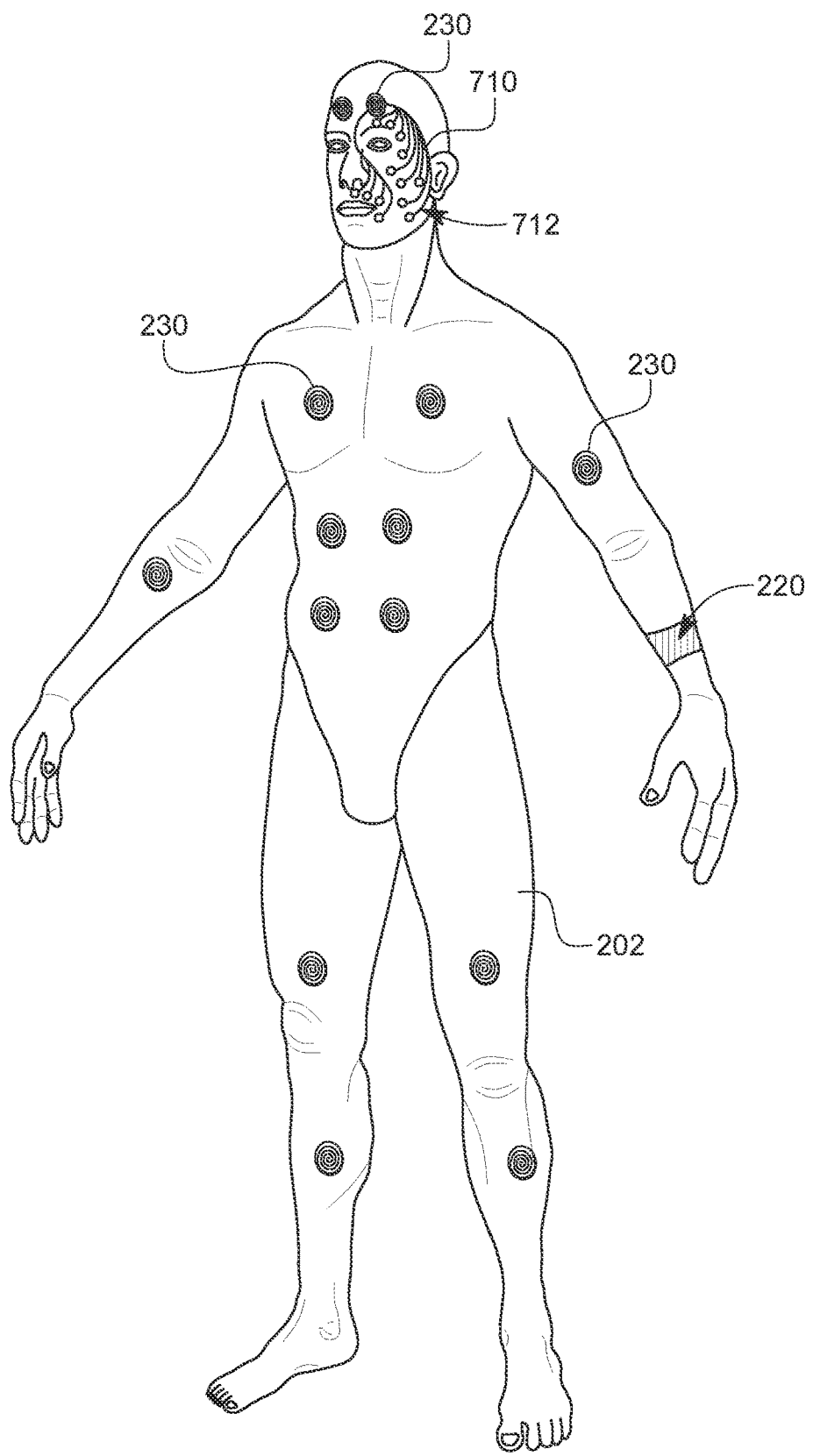
FIG. 7 illustrates an implementation of the system of FIG. 2 in which the single electrode sensor may be configured to have satellites electrodes.

As shown in FIG. 7, the SISO-BCC sensor 230 can also be used to collect measurements from smaller electrodes 712 (called satellite electrodes herein), placed in its proximity. Such satellite electrodes 712 can be designed as tattoo electrodes, and electromyograms obtained from them are transmitted by the SISO-BCC electrode 230. This kind of application is especially useful to improve the user's quality experience. It is also useful to reduce the required number of SISO-BCC electrodes and related monetary costs. For this implementation, there is a wired connection 710 between the sensor 230 and the satellite electrodes 712. The wired connection 710 may be as thin as a piece of paper, as copper lines are formed on a flexible substrate (e.g., polyimide). In this embodiment, the satellite electrodes 712 cannot receive or emit RF signals, and thus, they cannot harvest RF energy. These sensors 712 are configured to receive their energy from the sensor 230, along the wires 710.

Therefore, the RF-EH functionality of the WExG system 200 shown in FIG. 2 is available only for the sensors 220 and 230, and only these sensors are able to harvest ambient RF signals' energy from uplink and downlink communications of several technologies. Such technologies may include but are not limited to a) Wi-Fi and cellular signals to/from a smartphone and/or smartwatch, b) Bluetooth signals to/from an earphone, smartwatch, and/or smartphone, and c) using the wireless charging standard capability of a smartwatch and/or smartphone, such as near field communication (NFC). Thus, in case of insufficient energy arrival due to the lack of ambient RF signals, the sensor pings the hub to provide RF signals for recharging its energy storage device. In one embodiment, the hub may be configure to signal the user to charge the electrodes by placing the hub closer to the sensors. In this embodiment, the charging of the sensors 220 and/or 230 from the hub 210 does not happen automatically, but requires approval from the user of the hub. One or more of the WExG components can also be charged through a universal serial bus (USB) powered wireless charging pad 270, as shown in FIG. 2.

The performance of the system 200 was evaluated as now discussed. For this test, a time-slotted medium access control (MAC) protocol was used. Since several ExG modules are allowed to transmit at the same time slot, collision avoidance is necessary to provide ultra-reliable and low-latency communication (URLLC) to/from the hub. In this regard, the BCC module 322 employs a successive interference cancelation (SIC) method to enable simultaneous transmission from multiple ExG nodes 220/230. However, the performance obtained by each active ExG node is primarily determined by the received signal strength (RSS) from all active ExG nodes. Noting that the RSS is determined by both transmission power and channel gain, the optimal power allocation level will be different for different combinations of active sets of ExG nodes.

In this regard, the ExG nodes 220/230 that need to send data to the hub 210, first send a request-to-send (RTS) signal including their node identification (ID) along the BCC channel 210-230. Each node in the system 200 has a unique ID. Based on the active set of ExG nodes 220/230, the hub 210 broadcasts a clear-to-send (CTS) signal (also along the BCC channel 210-230) that includes the IDs of access granted ExG nodes as well as their transmission level. Based on the determined transmission power levels, the active ExG nodes that were granted access, start transmitting data packages along the BCC channel 210-230, as schematically illustrated in FIG. 8. The hub 210 creates a table of optimal power allocation, whose size is the same as the number of node combinations, i.e., 2N, where N is the total number of ExG nodes 220/230 in the system 200. The related entries of this table are updated if there is any significant change in the BCC channel conditions, which can be estimated and identified based on the RSSI levels during the RTS period.

Figure 9A:
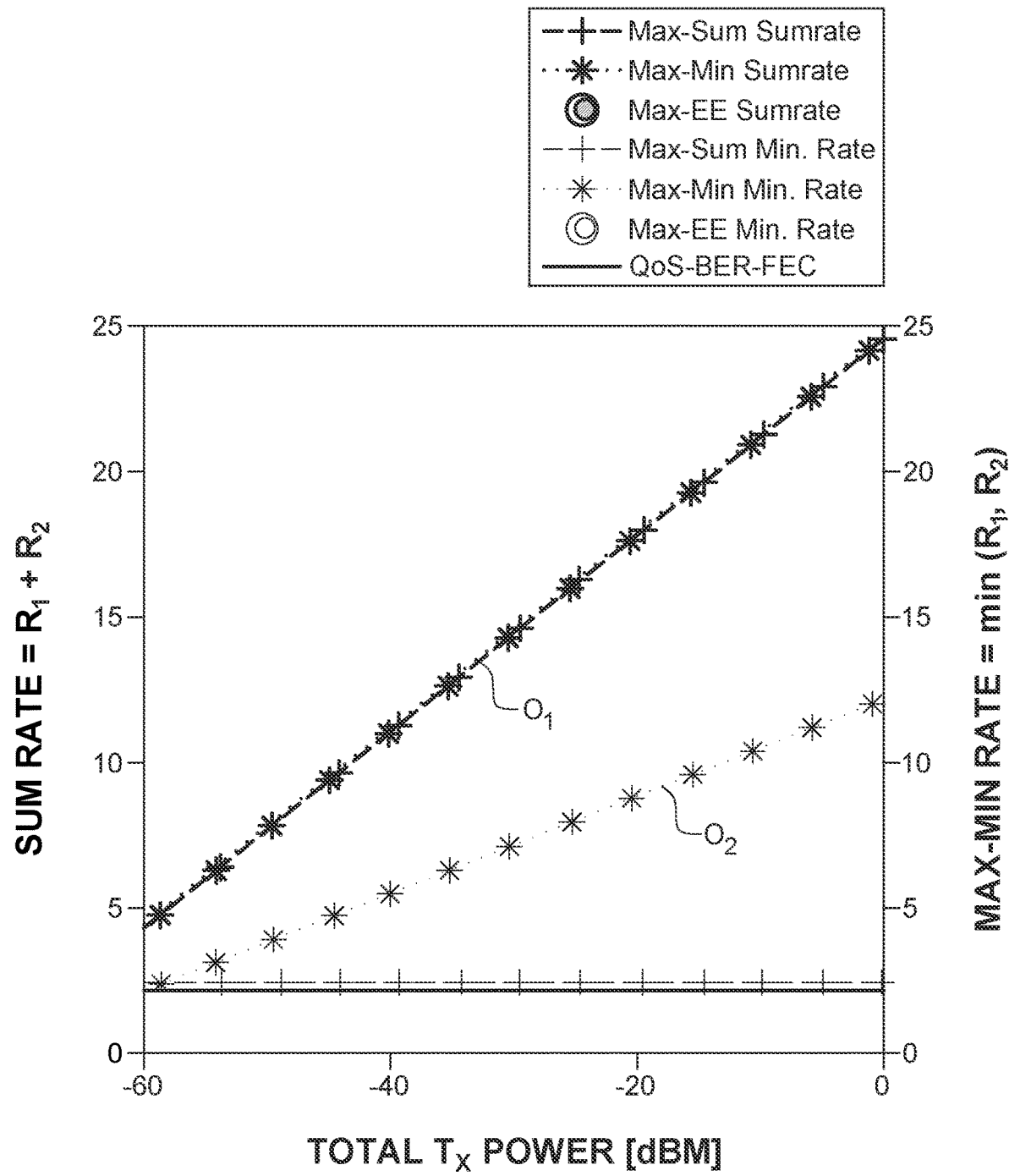
FIGS. 9A and 9B illustrate the energy efficiency of the system of FIG. 2 when transmitting the data over the body communication channels.
Figure 9B:
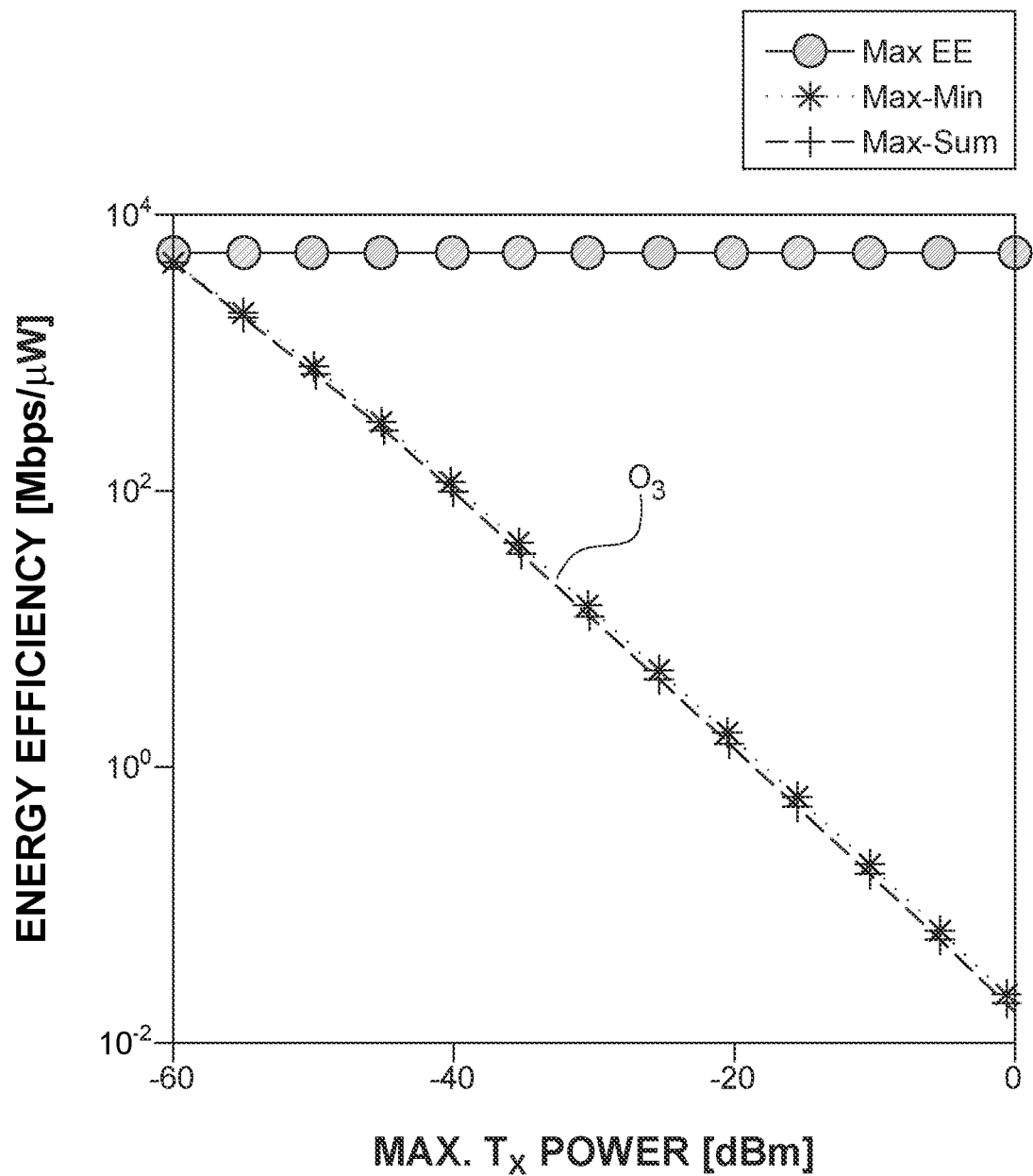

The hub 210 can also create separate table objectives, for example, the performance of two ExG nodes located 80 cm and 90 cm away from the hub 210. For example, three possible objectives are: O1) maximum sum-rate (see FIG. 9A), O2) max-min fairness (see FIG. 9A), and O3) maximum energy efficiency (see FIG. 9B). FIG. 9A shows on the left y-axis the sum-rate [R=R1+R2] while the right y-axis shows the max-min rate [R=min (R1, R2)]. Although the sum-rate of the system is almost the same under O1 and O2, the O2 is fairer between the nodes as R1=R2 all the time. On the other hand, O3 in FIG. 9B makes sure that both ExG nodes achieve exactly the requested QoS threshold ($\approx$2 Mbps). An observation that can be drawn from FIG. 9A is that the BCC system can reach very high data rates at very low transmission powers. For example, the BCC system can provide more than 6 Mbps data rate at 1 μW transmission power. On the other hand, Bluetooth 5 can reach 1 Mbps and 2 Mbps data rate by transmitting at 10 mW and 100 mW power levels, respectively. The energy efficiency of the ExG system at various transmission power is illustrated in FIG. 9B, where the energy efficiency objective reaches several Mbps/pW power efficiency levels at 2 Mbps, which is expected to be much higher if lower QoS levels are needed. Indeed, 2 Mbps can be regarded as a high-speed especially when sampling frequency of typical health monitoring systems are considered. However, high data rate achievability of the system is still desirable for application with URLLC requirement.

Figure 10:
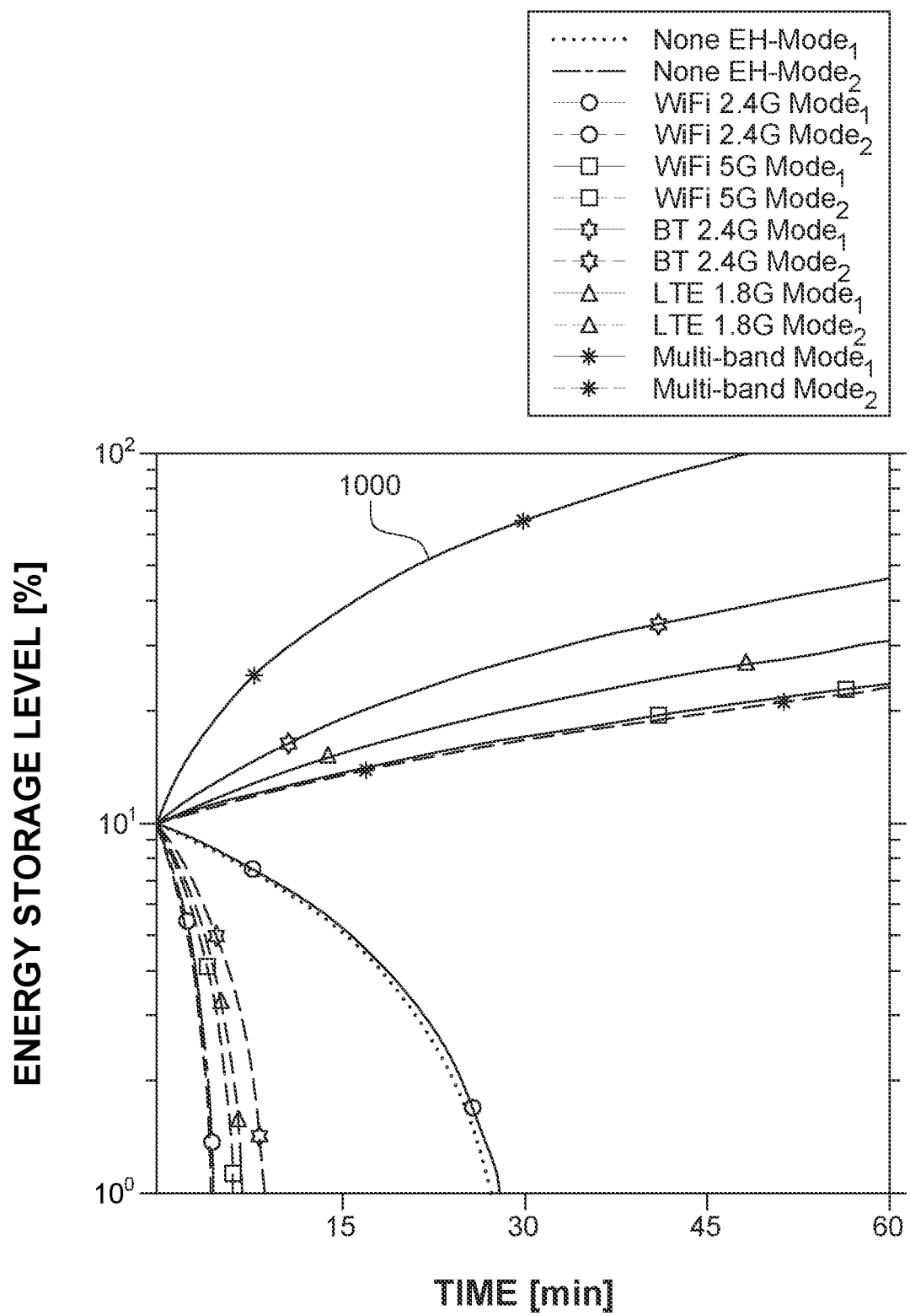
FIG. 10 illustrates the charging trend for the sensors of the system in FIG. 2 when the sensors harvest energy from ambient devices.
Figure 11A:
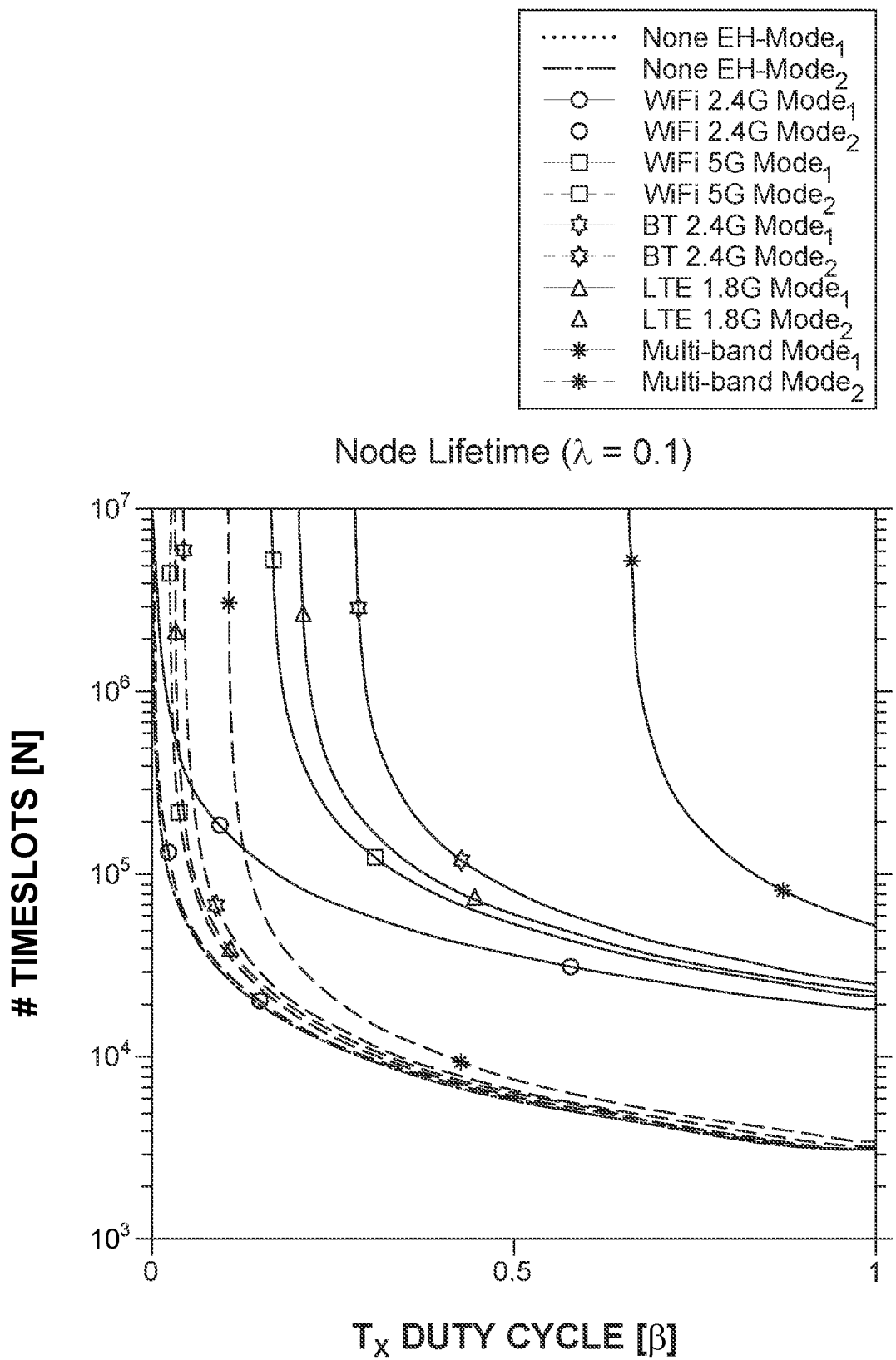
FIGS. 11A to 11C illustrate the sensors' life time when charged exclusively with energy harvested from the ambient devices.
Figure 11B:
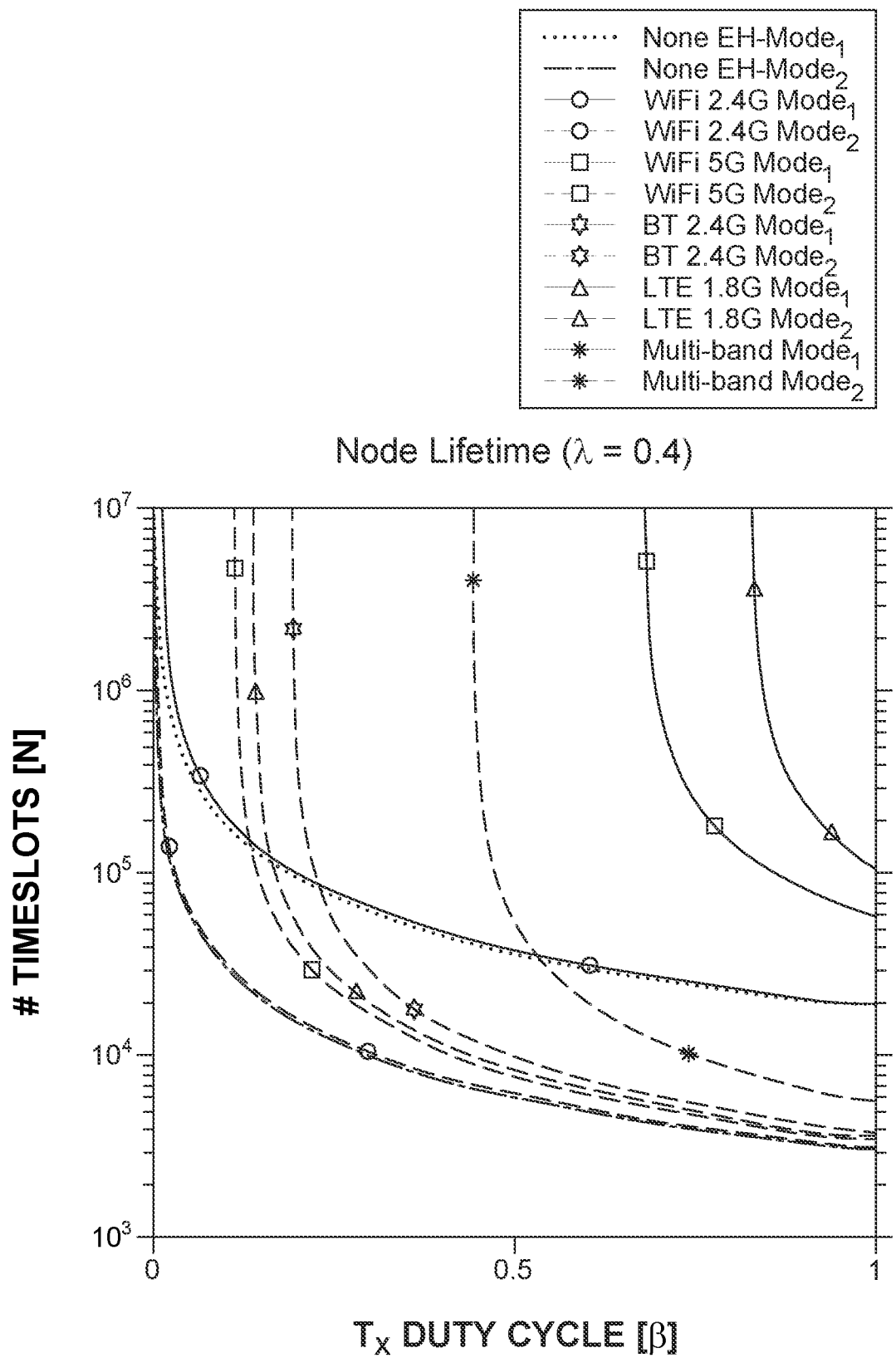
Figure 11C:
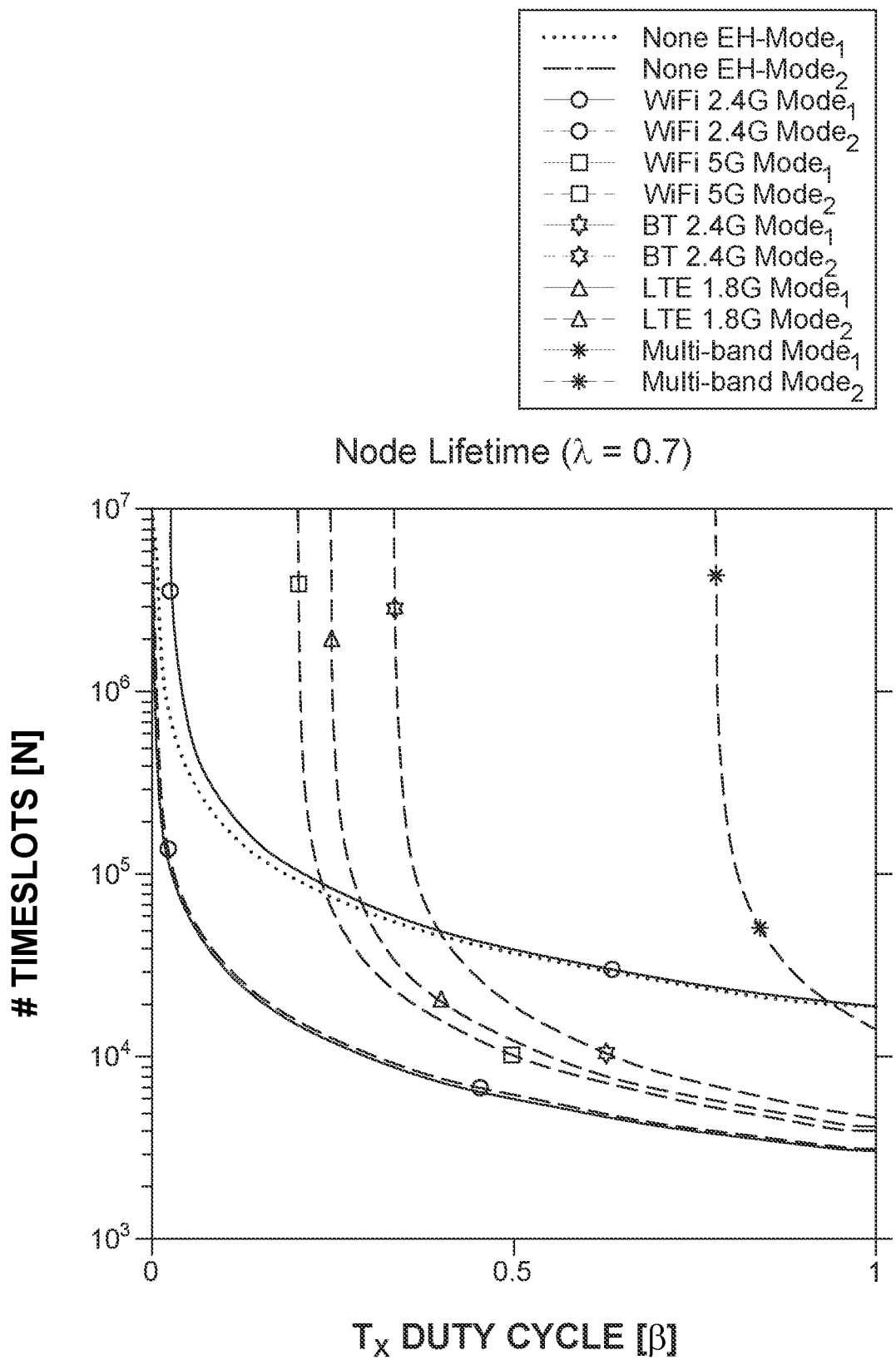

For the energy harvesting trend, which is illustrated in FIG. 10, and the node lifetime, which is illustrated in FIGS. 11A to 11C, an ECG application was considered with system-on-chip (SoC) ECG and accelerometer. A similar system with BLE capabilities for data transmission was used, and the energy consumption for two different modes of operation is as follows:

3.7 V, 0.5 mA: In the first mode, the heart rate detected by the ECG-SoC is transmitted through the BLE, which consumes the 96% of the overall energy consumption, i.e., 1.85 mW.

3.7 V, 1 mA: In the second mode, the heart rate and acceleration sampled at 40 Hz frequency are streamed through BLE, which consumes the 88% of the overall energy consumption, i.e., 3.7 mW.

Next, in addition to the BCC transmission power, the inventors also accounted for 74 μW and 444 μW SoC energy consumption in the first and second modes, respectively. The following RF energy sources were considered to be present around the human subject 202 during the tests:

1. A 5 meters away Wi-Fi router operating at 2.45 GHz,
2. A 0.5 meter away smartwatch operating on Wi-Fi 5 GHz,
3. A 0.5 meter away Bluetooth headphone operating on 2.45 GHz, and
4. A 1 meter away smartphone operating on 1.8 GHz cellular band.

While a single-band wireless energy harvester (WEH) can be designed for one of this energy sources, a multi-band WEH can be designed to harvest from all of them. Both of these possibilities are now considered. It is assumed that both the single-band and multi-band rectenna have a power conversion efficiency of 0.7. The harvested energy is stored to a solid-state capacitor of 1.3612 Joules. In order to observe the charging trend and node lifetime, two duty cycles are defined:

A. $0 \leq \lambda \leq 1$: The duty cycle of the RF energy sources, which determines the energy arrival rate.
B. $0 \leq \beta \leq 1$: The duty cycle of the ExG node, which determines the energy departure/consumption rate.

Based on an initial %10 battery capacity, FIG. 10 shows the charging trend for $\lambda=0.5$ and $\beta=0.5$ at different modes of operation. Excluding the first source (Wi-Fi at 2.45 GHz, 5 m away), all energy sources were able to achieve a positive charging trend in the first mode. This shows that the RF devices in the close-proximity of the human subject (e.g., smartwatch, phone, headphones, and other wearables) can provide sufficient energy for charging the energy storage device of the sensors 220/230. However, none of these sources can provide more energy than the second modes' energy consumption. At this point, the multi-band energy harvesting 1000 was able to yield a positive charging trend, which shows the benefit of multi-band WEH.

Based on an initial %100 battery capacity, FIGS. 11A to 110 show the node life time based on various energy arrival and departure rates. These figures show that the WEH-ExG devices 220/230 can reach an energy self-sufficient state if the energy arrival and departure rates are above and below certain thresholds, based on the energy consumption and RF energy source transmission power levels. The above experiments do not take into consideration the capability of the sensors 220/230 of requesting the hub to generate RF signals on-demand, which will further improve the energy storage efficiency.

As previously discussed, the embodiments illustrated herein apply to any WExG application. Therefore, the system 200 can have widespread use for physiotherapy and rehabilitation in the health care industry. The implementation of the system 200 is also a promising candidate for a rapidly developing fitness and wellness tracking sector as well as sports conditioning of athletes. The entertainment industry is also a potential user of the system 200 as most animation movies are created by placing electrodes to capture mimics, gestures, and body postures of highly talented actress/actors. This is generally implemented through wired electrodes, which pose wiring complexity to film crew and discomfort to actress/actors. Moreover, the wireless WExG is also one of the key technologies for virtual reality (VR) and augmented reality (AR) applications. Another promising usage of the system 200 is in the field of biomechanics and prosthetic organs, where a mechanical prosthetic limb, for example, can be controlled using the BCC channels, by applying the muscle signals collected with the sensors 220/230 from one region of the body. This is advantageous as the current applications typically use wired EMG sensors, limiting the user's mobility due to the cabling complexity. On the other hand, RF-based EMG sensors generally have a large form factor due to the battery size and RF-front end requirements. Thus, the system 200 can be applied to a wide range of application that currently use wired system, to make the user's experience more comfortable.

Figure 12:
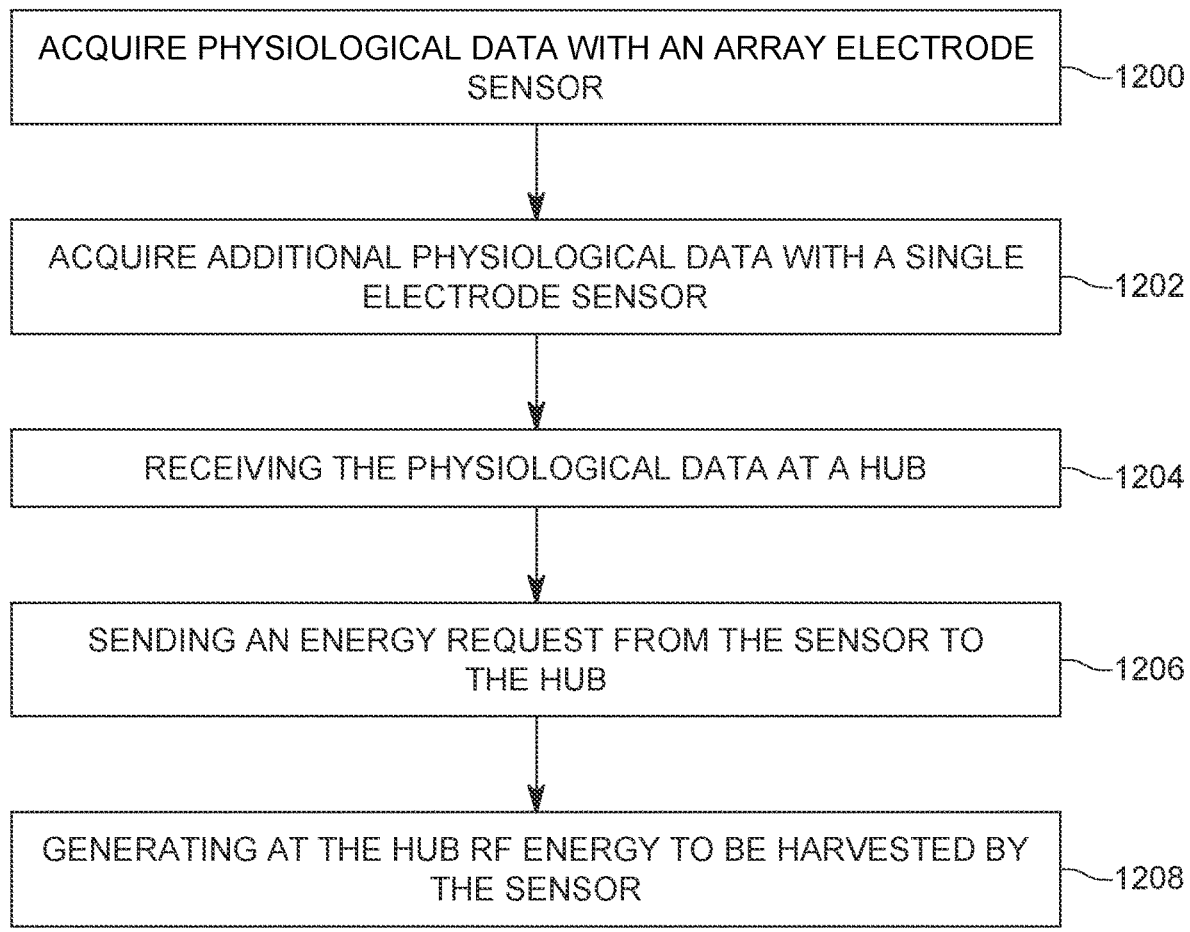
FIG. 12 is a flow chart of a method for acquiring physiological data with the system illustrated in FIG. 2.

A method for collecting physiological data with the acquisition system 200 illustrated in FIG. 2 is now discussed with regard to FIG. 12. The method includes a step 1200 of acquiring physiological data with an array electrode sensor 220 placed on a human skin, the array electrode sensor having plural electrodes 314, a step 1202 of acquiring additional physiological data with a single electrode sensor 230 placed on the human skin, the single electrode sensor having a single electrode 626. It is noted that in one embodiment, only one step of the steps 1200 and 1202 needs to be performed. In one application, the additional physiological data may be different from the physiological data. The method further includes a step 1204 of receiving the physiological data from the array electrode sensor 220 and/or the additional physiological data from the single electrode sensor 230, at the hub 210, but only along the BCC channels. In other words, the system 200 is configured in this embodiment to exchange the acquired data only through the BCC channels, to ensure the confidentiality of the transmission. This means that in this embodiment, the sensors 220 and/or 230, although having RF antennas, are not configured to exchange data through the RF antennas. The method may further include a step 1206 of sending an energy request signal 231 from at least one of the array electrode sensor 220 and the single electrode sensor 230 to the hub 210, along the BCC channels. In one application, the sensors 220 and/or 230 may be configured and programmed to transmit only the energy request signal 231 through RF channels. In response to the received energy request signal 231, the hub 210 emits in step 1208 RF signals 261, which are used by the at least one of the array electrode sensor 220 and/or the single electrode sensor 230 to harvest energy.

The disclosed embodiments provide a data acquisition system that can be attached to the human body and uses BCC channels for data communication and RF channels for energy harvesting. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

[1] U.S. Pat. No. 8,633,809

What is claimed is:

1. A physiological data acquisition system comprising:
an array electrode sensor having plural electrodes and configured to acquire physiological data;
a single electrode sensor having a single electrode and configured to acquired additional physiological data; and
a hub that is configured to receive the physiological data from the array electrode sensor and the additional physiological data from the single electrode sensor only along body communication channels,
wherein at least one of the array electrode sensor and the single electrode sensor is configured to send an energy request signal to the hub, along the body communication channels, and
wherein the hub, in response to the received energy request signal, emits radio frequency signals, which are used by the at least one of the array electrode sensor and the single electrode sensor to harvest energy.

2. The system of claim 1, wherein each of the array electrode sensor and the single electrode sensor has an energy storage device, and a processor, and the processor is configured to determine an energy level in the energy storage device, and initiate the generation of the energy request signal.

3. The system of claim 1, wherein each of the array electrode sensor and the single electrode sensor has a body communication channel module configured to transmit the physiological data through the body communication channels.

4. The system of claim 3, wherein the body communication channel module of the array electrode sensor is configured to use a first set of the plural electrodes for acquiring the physiological data and a second set of the plural electrodes for transmitting the physiological data to the hub, along the body communication channels.

5. The system of claim 4, wherein the body communication channel module is configured to simultaneously acquire the physiological data with the first set and transmit the physiological data with the second set.

6. The system of claim 3, wherein the body communication channel module of the array electrode sensor uses the first and second sets of the plural electrodes in a multiple-input multiple-out (MIMO) configuration.

7. The system of claim 6, wherein the body communication channel module of the single electrode sensor uses the single electrode in a single-input single-output (SISO) configuration.

8. The system of claim 7, wherein the plural rectennas are not configured for data exchange.

9. The system of claim 7, wherein an energy received by the plural rectennas is transformed into electrical energy and stored in an energy storage device.

10. The system of claim 1, wherein the array electrode sensor has plural rectennas, each one configured to receive a given radio frequency band.

11. The system of claim 1, wherein the hub comprises:
a strap to be attached to a body;
a casing connected to the strap and configured to act as a reference electrode; and
plural electrodes configured to receive the physiological data and the additional physiological data along the body communication channels.

12. The system of claim 11, wherein part of the plural electrodes is placed on the casing and another part is placed on the strap.

13. The system of claim 1, wherein the hub is a smartphone, and the physiological data is electromyography data.

14. A physiological data acquisition system comprising:
an array electrode sensor having plural electrodes and configured to acquire physiological data; and
a smartphone that is configured to receive the physiological data from the array electrode sensor only along body communication channels,
wherein the array electrode sensor is configured to send an energy request signal to the smartphone, along the body communication channels, and
wherein the smartphone, in response to the received energy request signal, emits radio frequency signals, which are used by the array electrode sensor to harvest energy.

15. The system of claim 14, wherein the array electrode sensor has an energy storage device, and a processor, and the processor is configured to determine an energy level in the energy storage device, and generate the energy request signal.

16. The system of claim 14, wherein the array electrode sensor has a body communication channel module configured to transmit the physiological data through the body communication channels.

17. The system of claim 16, wherein the body communication channel module of the array electrode sensor is configured to use a first set of the plural electrodes for acquiring the physiological data and a second set of the plural electrodes for transmitting the physiological data to the hub, along the body communication channels.

18. The system of claim 17, wherein the body communication channel module is configured to simultaneously acquire the physiological data with the first set and transmit the physiological data with the second set.

19. The system of claim 16, wherein the body communication channel module of the array electrode sensor uses the first and second sets of the plural electrodes in a multiple-input multiple-out (MIMO) configuration.

20. The system of claim 14, wherein the array electrode sensor has plural rectennas, each one configured to receive a given radio frequency band, an entire energy received by the plural rectennas is transformed into electrical energy and stored in an energy storage device, and the plural rectennas are not configured for data exchange.

* * * * *